US009623285B1

(12) United States Patent
Ruiz

(10) Patent No.: US 9,623,285 B1
(45) Date of Patent: Apr. 18, 2017

(54) BARBELL LEVEL INDICATOR

(71) Applicant: Mariano M Ruiz, Knoxville, TN (US)

(72) Inventor: Mariano M Ruiz, Knoxville, TN (US)

( * ) Notice: Subject to any disclaimer, the term of this patent is extended or adjusted under 35 U.S.C. 154(b) by 227 days.

(21) Appl. No.: 14/454,797

(22) Filed: Aug. 8, 2014

Related U.S. Application Data

(60) Provisional application No. 61/863,970, filed on Aug. 9, 2013.

(51) Int. Cl.
*A63B 24/00* (2006.01)
*A63B 21/072* (2006.01)

(52) U.S. Cl.
CPC ........ *A63B 24/0062* (2013.01); *A63B 21/072* (2013.01); *A63B 2024/0068* (2013.01); *A63B 2220/40* (2013.01)

(58) Field of Classification Search
CPC ..... A63B 21/06; A63B 21/072; A63B 21/078; A63B 21/0783; A63B 24/0062; A63B 2024/0068; A63B 2220/16; A63B 2220/17; A63B 2220/24; A63B 2220/40; A63B 2220/44; A63B 2220/833; G01C 9/00; G01C 9/06; G01C 9/08
USPC ..... 33/366.11–366.27, 370–373; 482/1, 7, 8, 482/9
See application file for complete search history.

(56) References Cited

U.S. PATENT DOCUMENTS

| | | | |
|---|---|---|---|
| 4,888,875 A | | 12/1989 | Strother |
| 5,474,083 A | * | 12/1995 | Church ................. A61B 5/486 600/546 |
| 5,740,881 A | * | 4/1998 | Lensak .................... G01C 9/12 182/18 |
| 7,666,118 B1 | * | 2/2010 | Anthony ............ A63B 21/0724 482/104 |
| 7,743,520 B1 | * | 6/2010 | Jiorle ....................... G01C 9/28 33/366.11 |
| 7,819,785 B2 | * | 10/2010 | Maiaro ................ A63B 21/078 482/104 |
| 8,167,087 B2 | * | 5/2012 | Simeonov ............... E06C 7/003 182/18 |
| 8,714,013 B2 | * | 5/2014 | Watanabe ................ G01C 9/06 33/366.11 |
| 8,870,717 B2 | * | 10/2014 | Pfitzer .................. A63B 21/015 482/106 |
| 2004/0194329 A1 | * | 10/2004 | Drahos ..................... G01C 9/06 33/366.11 |

(Continued)

*Primary Examiner* — Loan H Thanh
*Assistant Examiner* — Gregory Winter
(74) *Attorney, Agent, or Firm* — Matthew M. Googe; Robinson IP Law, PLLC

(57) ABSTRACT

A barbell level indicator includes a housing shaped to fit adjacent a barbell, one or more magnets positioned within the housing for securing the housing to the barbell, a microprocessor positioned within the housing, an accelerometer secured within the housing for detecting data related to an angle and movement of the barbell, the accelerometer in electrical communication with the microprocessor, an alarm in electrical communication with the microprocessor for emitting a warning signal when an angle of the barbell is greater than a desired limit, and a short-range communications module in electrical communication with the microprocessor for transmitting the data related to an angle and movement of the barbell from the accelerometer to a mobile device.

11 Claims, 12 Drawing Sheets

(56) References Cited

U.S. PATENT DOCUMENTS

| | | | |
|---|---|---|---|
| 2006/0047232 A1* | 3/2006 | Bourne | A61B 5/1116 601/71 |
| 2008/0052934 A1* | 3/2008 | Hall | G01C 9/06 33/366.11 |
| 2011/0302796 A1* | 12/2011 | Schubert | G01C 9/06 33/366.11 |
| 2013/0288859 A1* | 10/2013 | Watterson | A63B 24/0062 482/8 |
| 2014/0295983 A1* | 10/2014 | Nooner | A63B 69/36 473/223 |
| 2016/0023043 A1* | 1/2016 | Grundy | A63B 24/0062 482/8 |

* cited by examiner

BARBELL LEVEL INDICATOR

CROSS-REFERENCE(S) TO RELATED APPLICATION(S)

This application claims priority to U.S. Application Ser. No. 61/863,970 to Mariano M. Ruiz for a "Barbell Level Indicator" which was filed on Aug. 9, 2013, the content of which is incorporated herein by reference in its entirety.

FIELD

This disclosure relates to the field of exercise training devices. More particularly, this disclosure relates to barbell level indicator for alerting a user when a barbell becomes unbalanced while exercising and for tracking data related to an exercise.

BACKGROUND

When exercising with weights in a gym, often a posture of a user and level of barbells are not correct. Experienced and novice weightlifters may be under a false impression that an accurate level of a barbell has been achieved and maintained.

While attempts have been made to create devices for assisting a weightlifter with proper posture and balance during a workout, such attempts have resulted in devices that do not adequately alert a weightlifter if a weight becomes unbalanced. For example, U.S. Pat. No. 4,888,875 describes a level for weightlifting that uses a liquid filled tube and ball for indicating a level. However, the device of the '875 Patent does not provide any feedback to a weightlifter and instead requires that the weightlifter view the device during exercise to determine whether balance is lost.

Further, with the advent of smartphones and wearable computing devices, users desire to track data relevant to particular exercises for self-improvement and sharing with friends.

What is needed, therefore, is a barbell level indicator to assist with maintaining a correct weightlifting posture and provide feedback to a weightlifter to increase strength and minimize injuries.

SUMMARY

Embodiments of the present disclosure provide a barbell level indicator for assisting a user with maintaining a correct posture and for providing feedback to a weightlifter. In a first aspect, the barbell level indicator includes a housing shaped to fit adjacent a barbell, one or more magnets positioned within the housing for securing the housing to the barbell, a microprocessor positioned within the housing, an accelerometer secured within the housing for detecting data related to an angle and movement of the barbell, the accelerometer in electrical communication with the microprocessor, and an alarm in communication with the microprocessor for emitting an warning signal selected from the group consisting of an audible alert or a light when an angle of the barbell is greater than a desired limit.

In one embodiment, the barbell level indicator further includes a short-range communications module in electrical communication with the microprocessor for transmitting data related to an angle and movement of the barbell from the accelerometer to a mobile device.

In another embodiment, the alarm is a buzzer alarm configured to emit an audible signal when an angle of the barbell is greater than a desired limit. In yet another embodiment, the alarm is one or more LED lights configured to illuminate when an angle of the barbell is greater than a desired limit.

In one embodiment, the barbell level indicator further includes a push button in electrical communication with the microprocessor for calibrating an initial angle of the barbell. In another embodiment, the short-range communications module comprises a Bluetooth® transmitter.

In a second aspect, a barbell level indicator is provided including a housing shaped to fit adjacent a barbell, one or more magnets positioned within the housing for securing the housing to the barbell, a microprocessor positioned within the housing, an accelerometer secured within the housing for detecting data related to an angle and movement of the barbell, the accelerometer in electrical communication with the microprocessor, an alarm in electrical communication with the microprocessor for emitting an warning signal selected from the group consisting of an audible alert or a light when an angle of the barbell is greater than a desired limit, and a short-range communications module in electrical communication with the microprocessor for transmitting the data related to an angle and movement of the barbell from the accelerometer to a mobile device.

In one embodiment, the alarm is a buzzer alarm configured to emit an audible signal when an angle of the barbell is greater than a desired limit. In another embodiment, the alarm is one or more LED lights configured to illuminate when an angle of the barbell is greater than a desired limit.

In a third aspect, a method of monitoring a barbell exercise is providing including the steps of: attaching a barbell level indicator to a barbell, the barbell level indicator including a housing shaped to fit adjacent the barbell, a microprocessor, an accelerometer in electrical communication with the microprocessor, and an alarm in communication with the microprocessor; calibrating the accelerometer such that an initial level of the barbell is stored on the barbell level indicator; storing a tolerance range of an angle of the barbell on the barbell level indicator; measuring a level of the barbell with the accelerometer; comparing a measured level of the barbell measured by the accelerometer with the initial angle of the barbell stored on the barbell level indicator with the microprocessor; and activating the alarm when a measured angle of the barbell exceeds the tolerance range of the barbell.

In one embodiment, the method further includes the step of storing data related to an acceleration of the barbell measured by the accelerometer. In another embodiment, the method further includes the step of counting a number of repetitions of the barbell that occur based on data stored related to an acceleration of the barbell. In yet another embodiment, the method further includes the step of transmitting data related to an acceleration and orientation of the barbell through a Bluetooth transmitter to a mobile device.

In one embodiment, the method further includes pairing a mobile device to the barbell level indicator via a short-range communications module. In another embodiment, the steps of calibrating the accelerometer and storing a tolerance range are performed on the mobile device. In yet another embodiment, the alarm is part of the mobile device, and wherein the mobile device activates the alarm based on data received from the barbell level indicator.

The barbell level indicator is composed with electronic components, a plastic enclosure, and mounting magnets. An accelerometer measures inclination, a microcontroller reads an analog output of the accelerometer and the firmware determines if the inclination is greater than a pre-set tolerance. If that is the case, an audible alarm and the LED's will indicate an error. A rechargeable circuit powers the electronic components. The device can be calibrated and contains several levels of sensitivity. Using a USB connection and/or communication through a short-range communications module such as a Bluetooth® transmitter, the device logs can be read to a computer for future analysis and progress study. The barbell level indicator enclosure is made of plastic and attaches to barbells using magnets. The barbell level indicator can be calibrated to maintain any angles and will not be altered if rolled around a bar. The barbell level indicator can be applied to numerous types of exercises performed with free-weights and some machines.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

DETAILED DESCRIPTION

Figure 1:
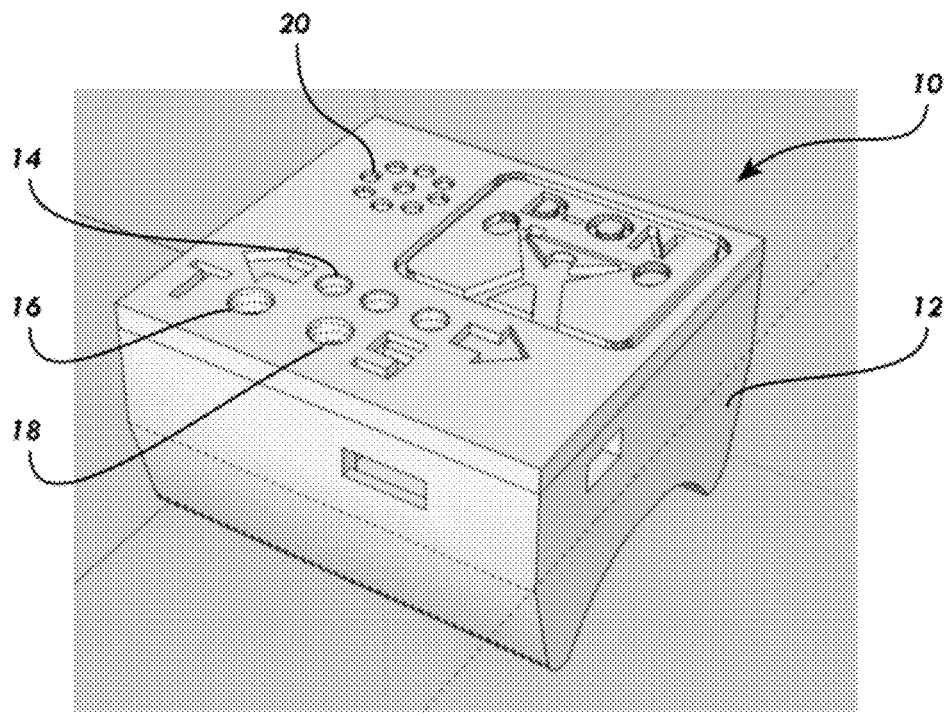
FIG. 1 shows a perspective view of a barbell level indicator enclosure according to one embodiment of the disclosure.

FIG. 1 shows a perspective view of a barbell level indicator 10 including an enclosure 12 having one or more LED openings 14, a tolerance button 16, a set point button 18, and a buzzer alarm aperture 20.

Figure 2:
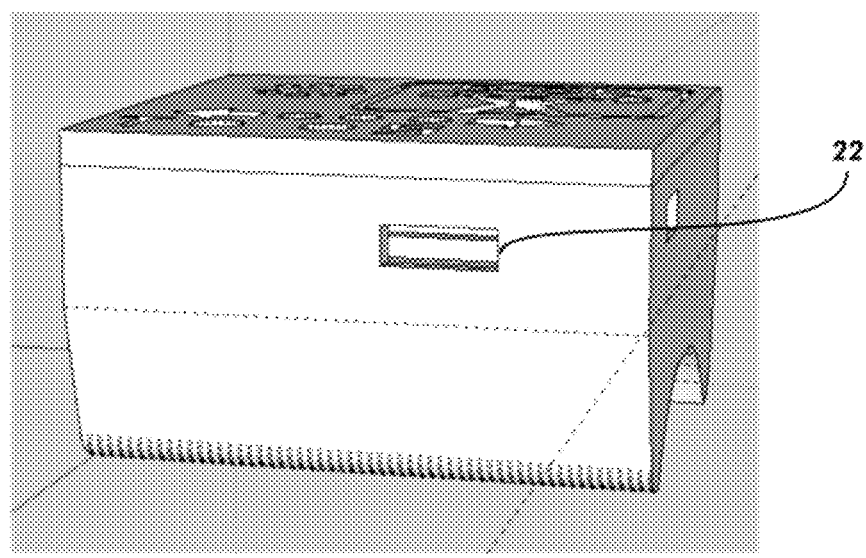
FIG. 2 shows a perspective view of the barbell level indicator according to one embodiment of the disclosure.

FIG. 2 is a front perspective view of the barbell level indicator 10 including a communication port 22, such as a USB interface. The communication port 22 serves two purposes. It serves as a wired communication bus, such as USB, between the memory of the barbell level indicator and a computer/tablet/mobile device. Secondly, the communication port 22 serves as a battery charger input.

Figure 3:
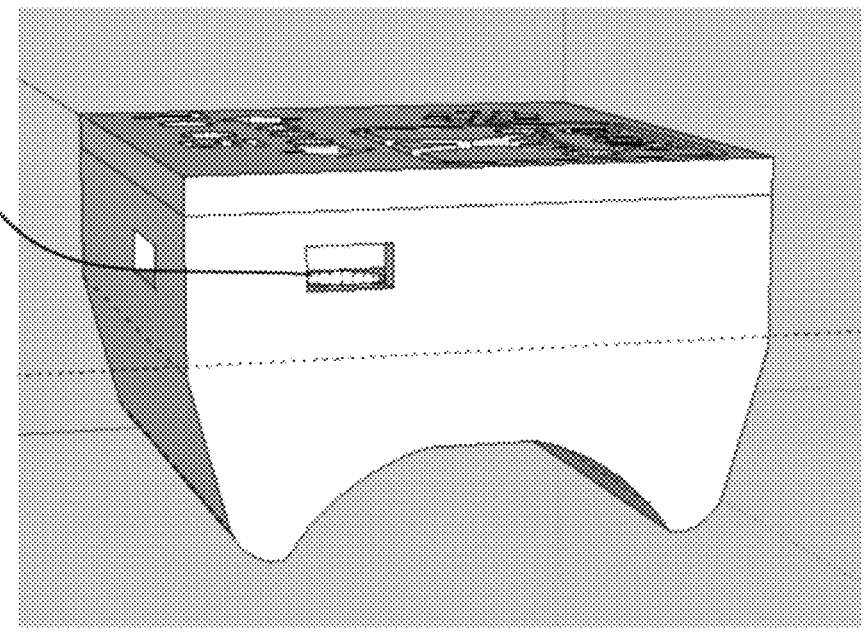
FIG. 3 shows a side view of the barbell level indicator according to one embodiment of the disclosure.

FIG. 3 shows a right side of the barbell level indicator 10 including an opening for the ON/OFF power switch 24 for the barbell level indicator 10.

Figure 4:
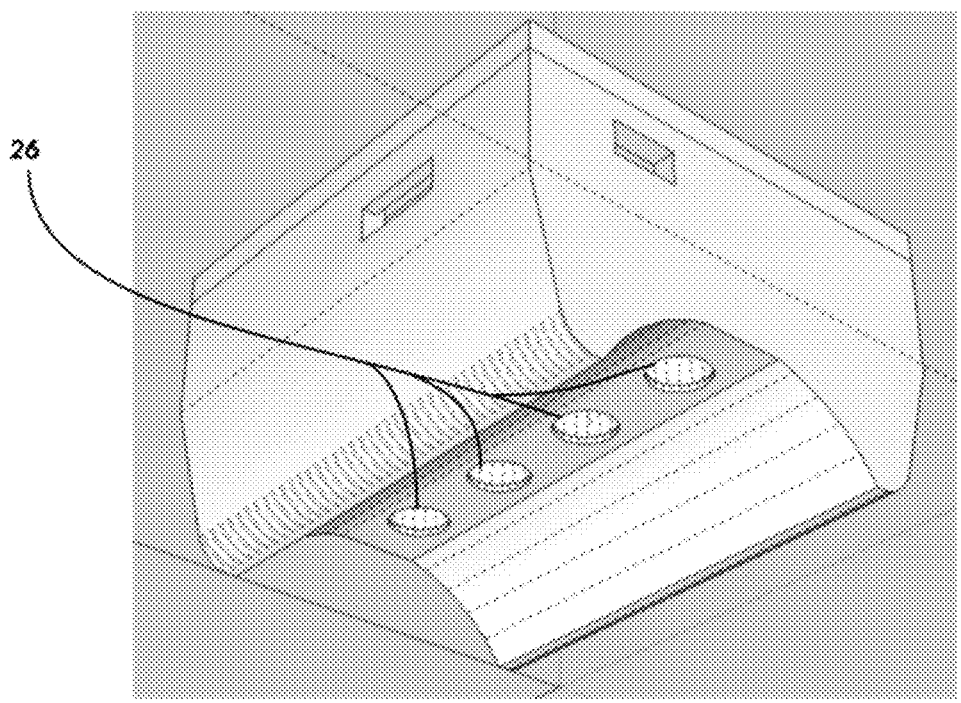
FIG. 4 shows a bottom view of the barbell level indicator according to one embodiment of the disclosure.

FIG. 4 shows a bottom view of the enclosure 12 including four apertures 26 containing one or more magnets for securing the barbell level indicator 10 to a surface, such as the surface of a barbell. The enclosure 12 includes a shaped bottom portion that is shaped to fit around a barbell, EZ curl bar, or trap bar with a diameter of approximately 30 mm. Alternatively, the enclosure 12 may be shaped to fit various other shapes such as a rectangular surface, flat surface, or other like geometric shapes.

Figure 5:
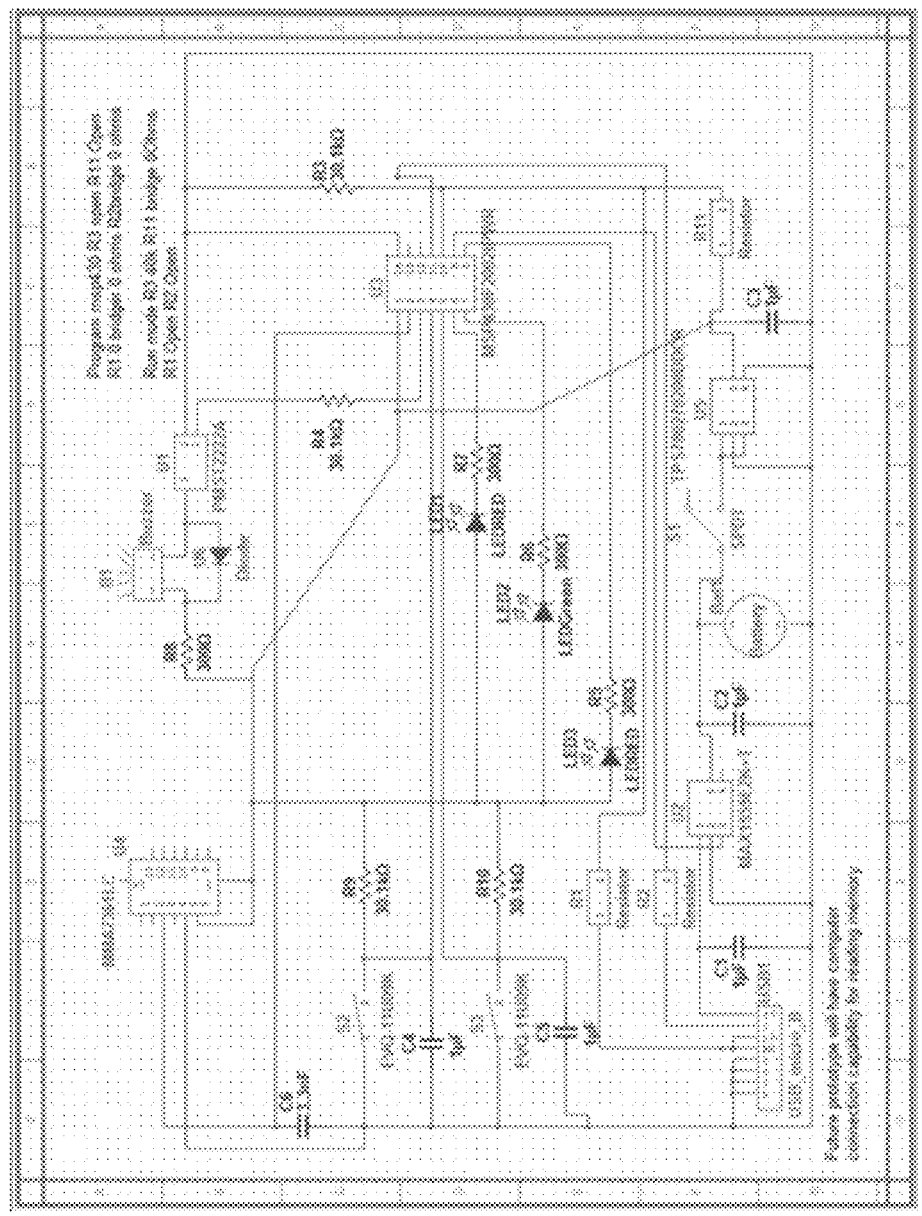
FIG. 5 shows an electronic diagram of electronic components of a barbell level indicator according to one embodiment of the disclosure.

FIG. 5 is an electronic diagram of a barbell level indicator including a USB USB1 or micro USB connector USB_micro_B used for recharging and data transfer. A transistor U1 is used to drive a buzzer alarm B1. The barbell level indicator 10 also includes Lithium Battery Charger chip U2, a Microcontroller U3 including firmware stored thereon, Input and Outputs. Accelerometer U4 provides an Analog output to the microcontroller U3 to determine a level of a barbell, Voltage Regulator U5 used to drop a voltage to a stable level for the electronics. A Rechargeable Battery BBat1 is preferably made of lithium Ion. Buzzer B1 is an alarm indicating out of tolerance, On/OFF switch S1, Tolerance button S2, Set point S3 used to calibrate an angle, Out of position 1 Red indicator LED1, within Tolerance Green Indicator LED2, Out of Position2 Red Indicator LED3. D1 is used to protect the buzzer reverse polarity voltages.

Figure 13:
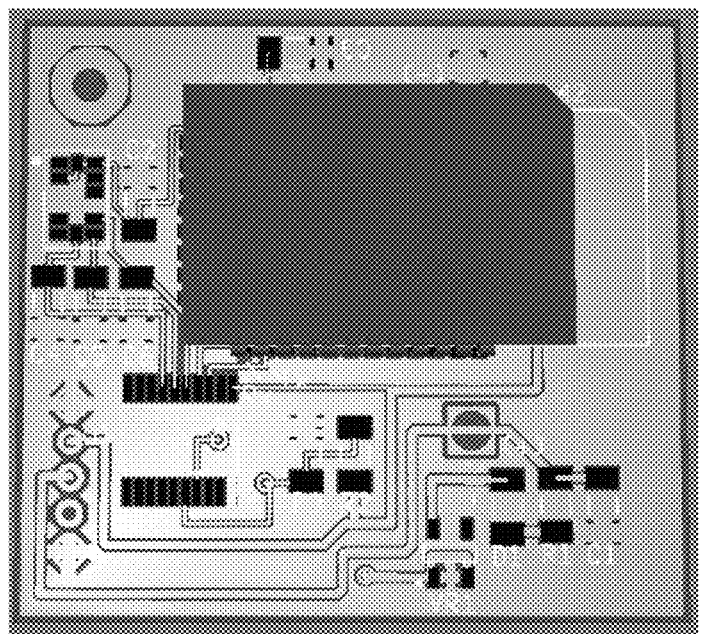
FIG. 13 shows an electronic diagram of a barbell level indicator including a short-range communications module according to one embodiment of the disclosure.
Figure 14:
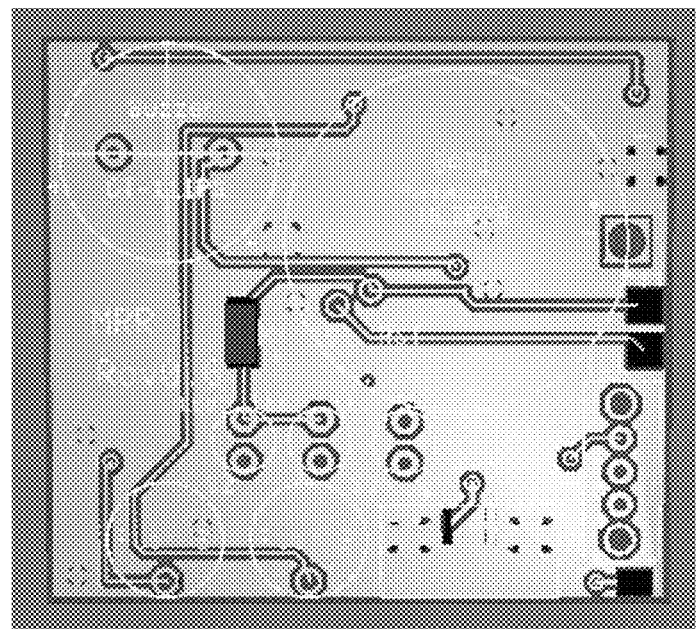
FIG. 14 shows an electronic diagram ground plane including components of the barbell level indicator according to one embodiment of the disclosure.
Figure 15:
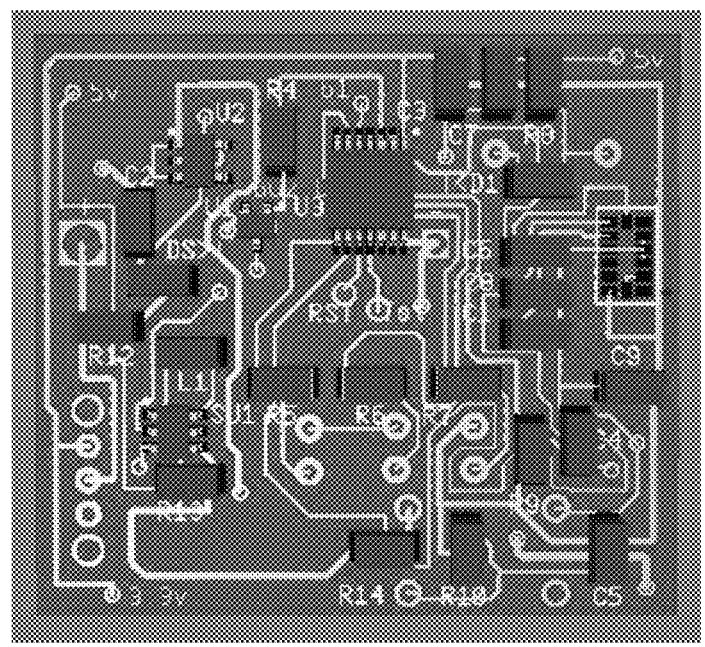
FIG. 15 shows an electronic diagram of a barbell level indicator including a voltage booster, charging circuit and accelerometer according to one embodiment of the disclosure.
Figure 16:
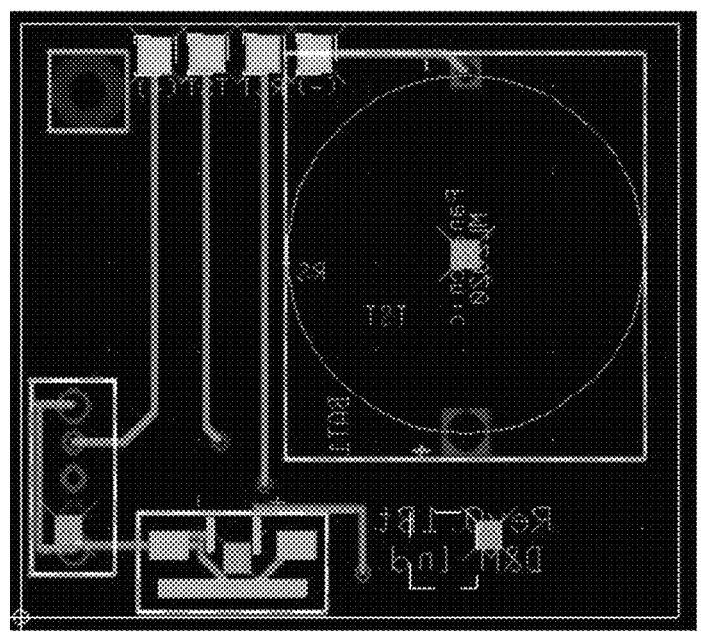
FIG. 16 shows an electronic diagram of a barbell level indicator including pins for firmware upgrades and ground planes according to one embodiment of the disclosure.
Figure 17:
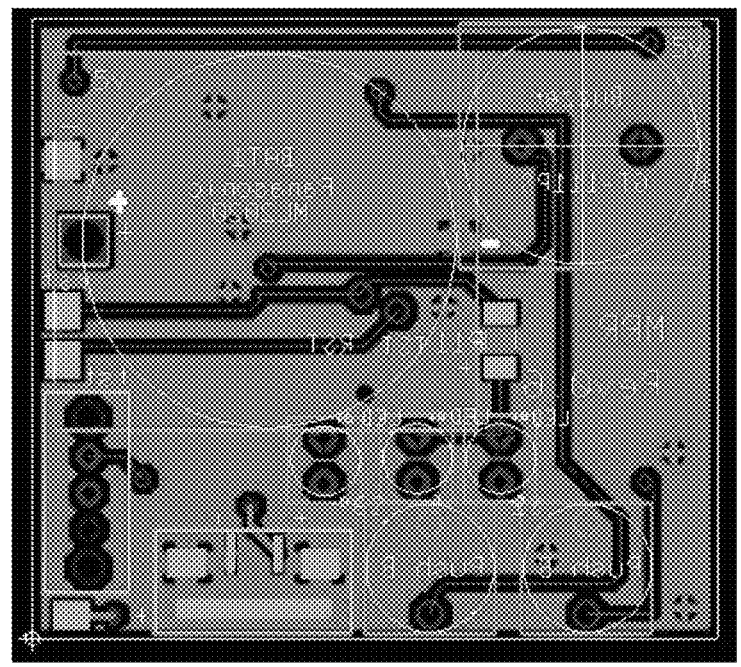
FIG. 17-19 show electronic diagrams of a barbell level indicator including a short-range communications module according to one embodiment of the disclosure.
Figure 18:
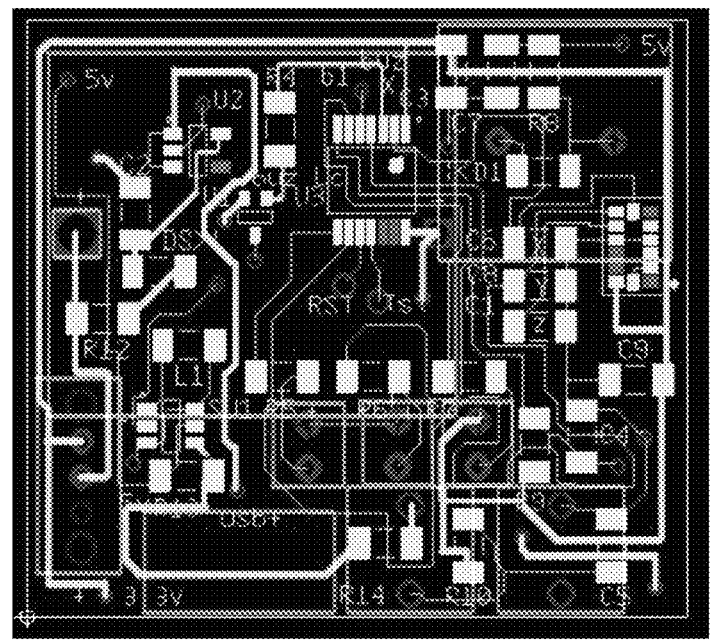
Figure 19:
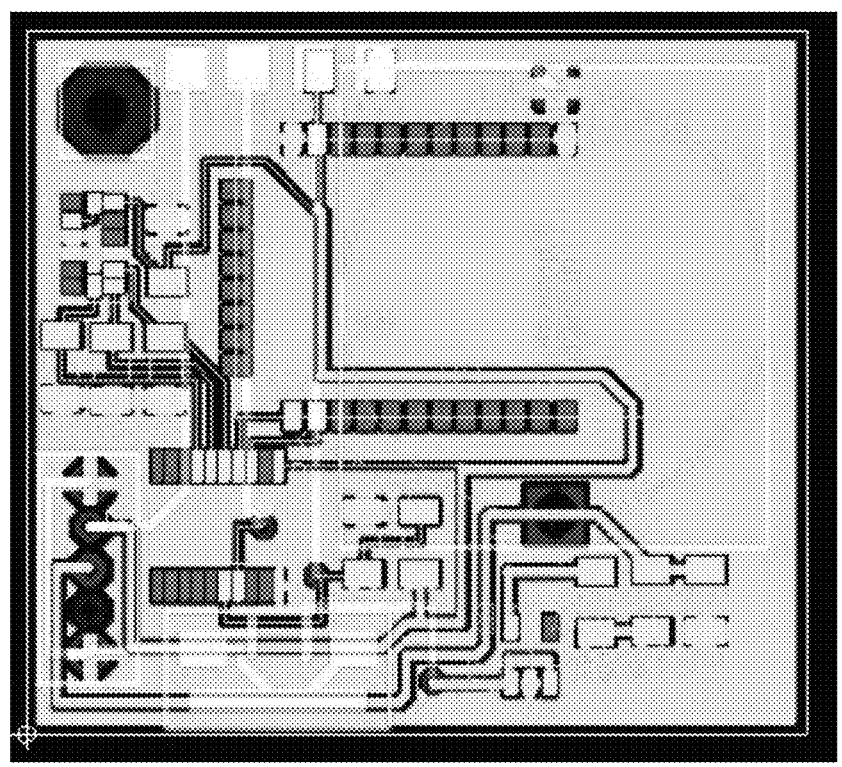

As shown in FIGS. 13-15, a short-range communications module, such as Bluetooth®, memory and a voltage booster can be included on the electronic diagram to increase sound, record and store values on memory, or transfer data wirelessly in real time from memory to a mobile device or a computer. The short range communications module enables the barbell level indicator 10 to communicate with a user's mobile device or personal computer, such as an iPhone® or Android® device, or other like devices such as a smartwatch, exercise device, or other personal computing device. The short-range communications module is preferably a Bluetooth® module. However other various protocols may be used such as Bluetooth® low energy (commonly referred to as Bluetooth® LE or Bluetooth Smart®). Various classes of Bluetooth® transmitters may be used such as, for example, Class 1, Class 2, or Class 3, wherein a range of the Bluetooth® transmitters varies depending on a class of transmitter used.

Charging Circuitry and Power Supply

The USB or micro USB connector receives power from a USB computer at 5 Volts, C1 Capacitor of 1 micro Farad is used to filter noise acting as a Bypass capacitor. Max1555EZK U2 is a USB 1 Cell Lithium Ion Battery Charger in package SOT25. The 5V coming from the USB pin 1 are connected to the battery charger chip on pin 1, Gnd shared through the circuitry is connected to pin2, Pin 3 on U2 connects to the microcontroller MSP430 U3 and goes low when the battery is charged. The output of U2 connects to Bat1 20 mm coin cell battery 3V positive terminal. The output of Bat1 goes thorough power switch ON/OFF. The switch serves as a way to turn on/off power to all the circuits after the battery. If the switch is on the ON position, the voltage regulator U5 Tps780 drops the voltage to 2.7 volts to maintain a constant voltage regardless of battery discharge. U5 pin1 connects receives the 3V voltage from the lithium Ion Battery on Pin 1, Common GND is connected to Pin 2 on the voltage regulator, Pin3 is used to enable the voltage regulator connected to 3V (Always enabled.) Pin4 on U5 is always connected to ground to default the voltage regulator to 2.7V. If Pin4 set high, a different lower voltage output is selected not useful in the circuitry. C3 a 1 microfarad capacitor is used as a bypass noise suppressing capacitor used to power the rest of the electronics. Additionally, the barbell level indicator can contain manganese Lithium Coin batteries that may be charged using a linear voltage regulator supplying 3.3V passing through a Shockley diode dropping the voltage to 3.1V and passing through a current limiting resistor.

Accelerometer Circuitry

The accelerometer U4 (such as part no. MMA7361LC available from Freescale Semiconductor) is an accelerometer capable of running at plus minus 1.5 g or plus or minus 6 g. The accelerometer is used to run on 1.5 g. It operates between 2.2V and 3.6 V. Our power source is at 2.7V in this case. It has three axis and we use axis X for leveling on pin3. The accelerometer outputs an analog signal proportional to the inclination of the barbell. Capacitor C6 of 3.3 nF is used as a bandwidth regulator for the accelerometer/decoupling capacitor connected to ground and the analog input on the microcontroller U3 pin2. Pin5 on the accelerometer is used to connect to common ground. Pin6 and Pin7 are connected to 2.7V coming from the voltage regulator. Pin6 receives the Positive Voltage used to power the accelerometer and Pin7 disables sleep mode on it by connecting to 2.7 Volts. On the next designs access to Y and Z axis will be connected also to a microcontroller to track upward acceleration and shift to both X and Y planes in the same manner. Potential alternative accelerometers may include, for example, part number LIS352AX is an accelerometer available from STMicroelectronics having the same footprint but may include different pin outs.

Buzzer Alarm

Figure 6:
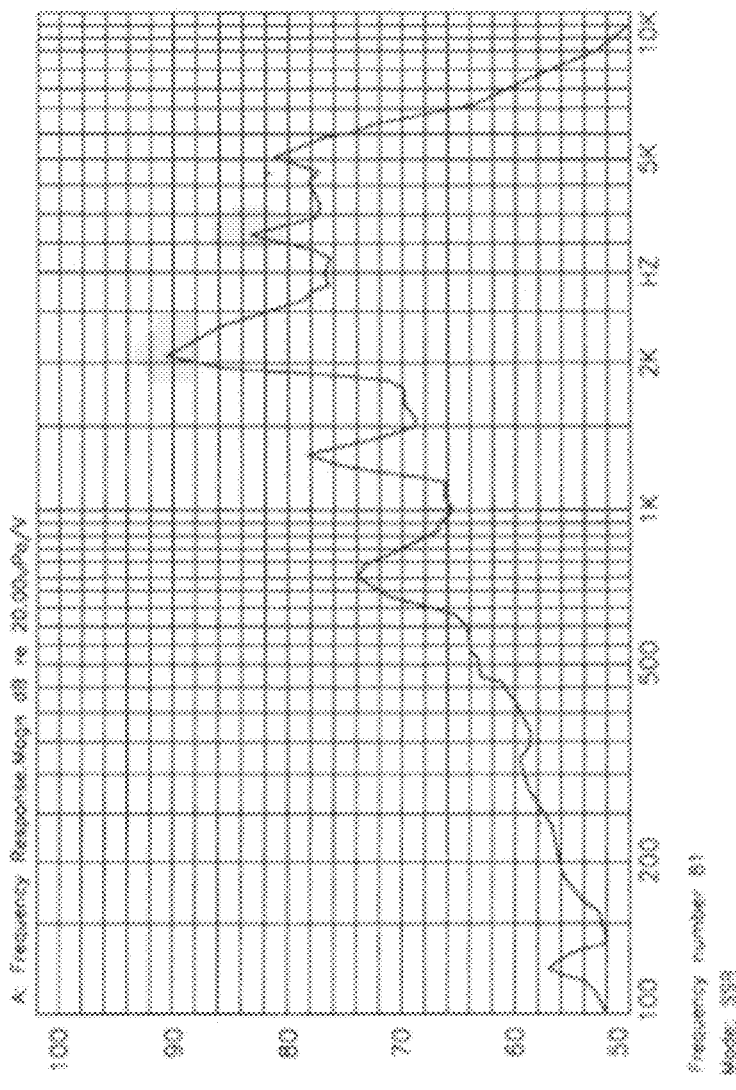
FIG. 6 shows a frequency graph according to one embodiment of the disclosure.

The buzzer alarm is powered using a transistor U1 PMST2222A BJT NPN. When the microcontroller U3 sets Pin3 high the base of the transistor at pin1 enables current flow from the 2.7V passing by R8 300 Ohm current limiting resistor, Buzzer pin1 output on buzzer pin2 entering transistor U1 on pin3 exiting to ground on pin2 and enabling the buzzer. D1 diode is used as a protection for voltage spikes when feeding a square wave to it. The piezoelectric buzzer operates on two frequencies shown on the graph of FIG. 6. Left alarm of the device sound at 2 KHz and the right Alarm sounds at 3 KHz. To increase the volume of the buzzer, a voltage booster may be used such as part number TPS61070-73 available from Texas Instruments. The voltage booster could replace a transistor, such as part number PMST2222A available from NXP Semiconductors. Step up voltage booster voltage is controlled using a voltage divider comprising two resistors using an inductor and one or more capacitors to increase the voltage up to 5V to increase a volume of the buzzer alarm.

LEDs

Light emitting diodes are connected to the microcontroller that sink the signal to ground to enable them. LED1 Anode connects to the 2.7V source passes by a current limiting resistor R7 of 300 ohms and to pin 6 on the microcontroller. The current limiting resistor limits to (2.7V–0.7V)/300. LED2 and R6 connect to Pin7, LED3 and R5 connect to Pin 8 on the U3 microcontroller. Led1 represents out of tolerance red light, LED2 represents within Tolerance, LED3 represents red out of tolerance.

Push Buttons

R9 of 30.1 KOhms acts as a current limiting resistor S2, C4 1 uF is used as a denouncing capacitor to allow switch denouncing when active. The signal from the switch denouncing circuit connects to Pin4 of the microcontroller. S3 momentary pushbutton R10 and C5 are replica of the first pushbutton circuitry connected to pin5.

Microcontroller

All the signals digital or analog connect to the micro controller. It runs at a speed of 1.1 Mhz with internal oscillator. The system is powered by the 2.7 Volts on pin1, ground connects on pin 14, Pin2 of U3 is set as analog input and reads the x-axis of the accelerometer, pin3 enables the transistor to power the buzzer, pin4 receives the momentary push button signal S2 (Tolerance), pin5 receives the momentary pushbutton signal of s3 (Setpoint calibration and no sound if hold) Pin7 Pin8 and Pin6 turn on the LEDs accordingly. The microcontroller may include universal asynchronous receiver/transmitter ("UART") capabilities and is configured to send data to an accelerometer or read commands from a personal computer or mobile device.

The microcontroller has two states, programming state and run state. In order to program the microcontroller RST pin10 and TST pin11 R3 and R11 need to be opened. The microcontroller is programmed using USB pin 2 connected to TST pin11 on the microcontroller using a 0 ohm resistor on R2. Pin 3 and 4 connect to RST pin 10 using a R1 bridged with a 0 Ohm resistor.

On run mode, R1 should be removed, R2 should be removed, and R11 should be bridge with 0 Ohms and R3 should be 30,100 ohms.

Programming

The microcontroller is made by Texas instruments msp430f2002 running at 1 MHz To program the microcontroller we use an msp430 Launchpad directly connected to the board. To read the inputs of the tolerance, set point and acceleration we use interrupts and polling.

10 Bits, enable reference voltage, setup reference voltage to use Vcc (2.7V) set sample channel P1.0

Setup Tolerance and Set Point Buttons Inputs Interrupts

Enable interrupt on P1.4 and P1.5 using edge detection and clear the interrupt flag as setup.

Setup all I/O.

P1DIR|=0x72;  //bit0=axis input bit1=buzzer output bit2=button output bit3=Calibrate out bit4=LED R bit5=LED G out bit6=LED B bit7=input out 0b01110010;

Set up Bluetooth communication settings( ) by defining RX, TX, CTS, RTS pins;
Set up Bluetooth XYZ MSB and LSB memory allocation.
Enable ADC on P1.0
This section starts the analog input acquisition of the accelerometer readings
Reset all outputs to off
Loop Begins
In the loop state, the microcontroller is polling accelerometer values and checking if the values are outside the tolerance to activate the buzzer alarm and activate appropriate LED's. Additionally, the microcontroller is listening for commands from the mobile device or personal computer (some of the available commands from the mobile device or personal computer include strings such as "e" for enable, "d" to disable accelerometer broadcast, "m" for reading memory values, "r" followed by an integer to set the rate to send values).
Accelerometer charging function ( )
If bit7 is high, go into a while loop blinking the red LED's indicating that the battery is charging. The program will not check for level changes and buttons will be disabled while charging.
shutoff ( )
If the program has been running for 15 minutes or more without detecting movement out of tolerance or commands through Bluetooth, go to sleep mode and only wake up if an input interrupt is detected or a power cycle. This function is made to save power. At this point, firmware also sends a shutting off command to connected Bluetooth devices.
Analog Input Read (Level)
The analog value is read by taking 20 number of samples of the analog value. The maximum number reached from the analog input can be 10 bits or 1024 decimal. To do the average we read the analog values and keep adding them in an integer and then dividing by the number of samples. This logic only works up to 16 bits or 65535.0 doing sampling we received a stable reading from the accelerometer. The analog values are read by interrupt triggers. Every time the interrupt is not called the microcontroller is in low power mode.
Set Buzzer and LEDs Accordingly
If the enable flag is true (Enable flag is set only by pressing the Tolerance or Set point buttons and stays latched until power cycled).
If the analogvalueaverage is greater than set point plus tolerance call the Buzz function. (The buzz function sets the piezoelectric buzzer to case selection one and led blink left and turn off all other LED's, In other words, the system is not leveled out of tolerance beeping and blinking the red left led.
If the analog value average is less than set point—tolerance. Call the buzz function and set case selection to 2 in order to get a different frequency and turn the right led on and all other LEDs are turned off.
If the analog value average is within the tolerance either positive or negative go to the function buzz selection case 3. Case 3 turns off all red LED's and piezoelectric blinking green led.
Button Pressed Interrupt
If the tolerance or set point are pressed we reset the shutoff counter to 0 to prevent from going to sleep. Latch the enable flag so the logic that alarms and turns on the LED's are enabled.
The Setpoint button serves two purposes. It calibrates to the current level and also if it is on hold for 5 seconds sets a flag to disable on the buzz function the sound and only allow LED's.

If the Setpoint button is on hold for five seconds, beep to indicate that the sound will be disabled. If the button is just pressed, the Setpoint will be loaded with the value of the current analog value average in order to calibrate that angle. The angle can be any degree excluding 90 degrees up or 180 degrees down.

If the tolerance button is pressed the tolerance is increased by the toladder variable and beep according to the level of tolerance until the maximum tolerance is reached and then the tolerance rolls back to case 1. The program has five tolerances. The most sensitive is tolerance 1.

Figure 7:
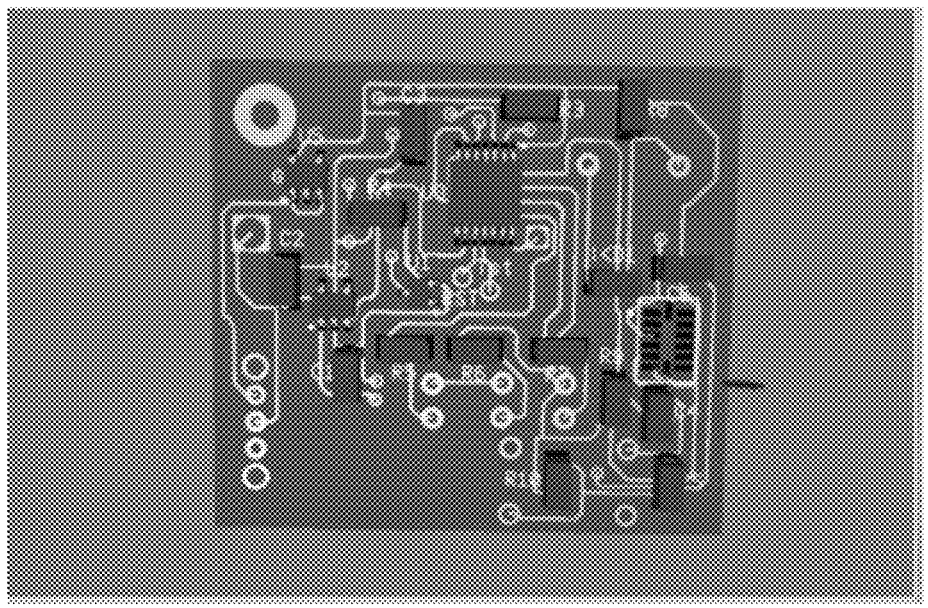
FIG. 7 illustrates the physical layout of the electronic components used on the bottom of the two-layer board according to one embodiment of the disclosure.

FIG. 7 illustrates a physical layout of the electronic components used on the bottom of the two-layer board. Most of the surface mount components are placed on this side. The main components shown on this picture are a microcontroller, accelerometer, battery charger module, voltage regulator, transistor to power buzzer noise filtering capacitors, pushbutton denouncing circuits, current limiting resistors and a reverse voltage diode protector.

Figure 8:
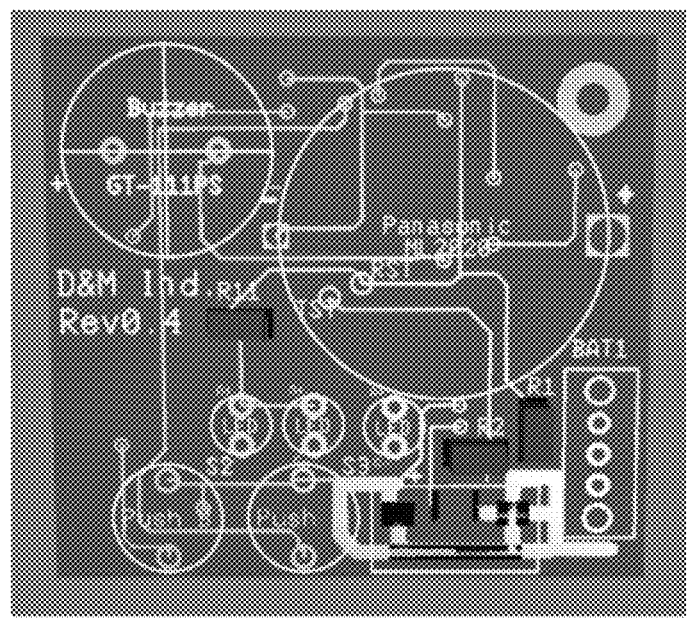
FIG. 8 illustrates the components silkscreen of the top of an electronic board according to one embodiment of the disclosure.

FIG. 8 illustrates a components silkscreen of a top of the board. The board contains a lithium ion rechargeable battery, piezoelectric buzzer, LED indicators, an ON/OFF switch, push buttons, programming resistors and a USB micro B connector.

Figure 9:
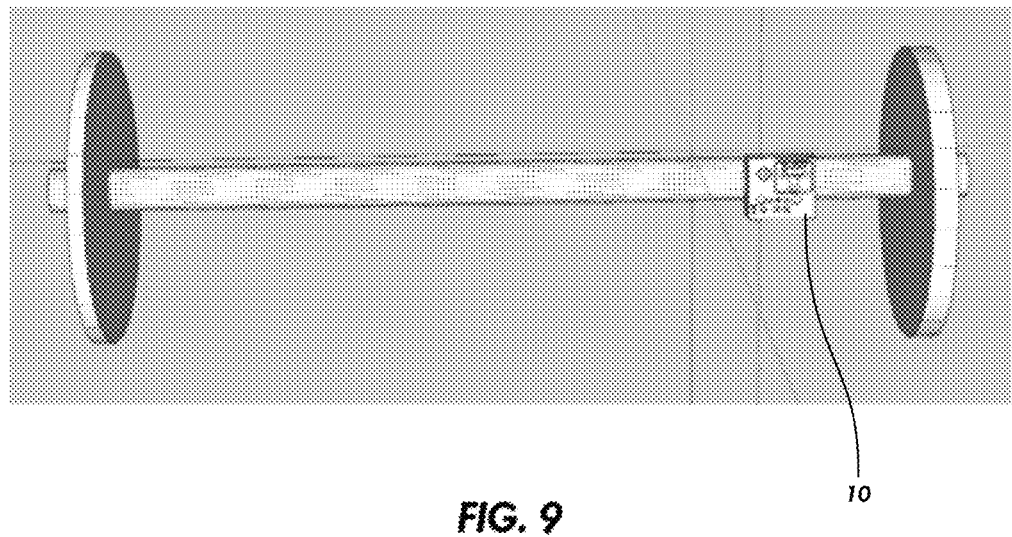
FIG. 9 shows a barbell on the floor, a setup typical for dead lifts, shrugs, curls, back pulls and other various exercises according to one embodiment of the disclosure.

When in use, the barbell level indicator 10 is removably connected to a barbell during a weightlifting exercise to alert a user when the barbell becomes out of balance. The barbell level indicator enclosure includes a curvature that substantially matches a curvature of the barbell. An inner portion of the barbell level indicator includes high strength round magnets ($\frac{1}{4}"\times\frac{1}{16}"$). The magnets are used to magnetically connect the barbell level indicator 10 to the barbell. Preferably, the barbell level indicator is mounted in a place visible to the user so that the user may view the LEDs of the barbell level indicator. However, audible tones emitted by the barbell level indicator also allow the indicator to be placed in a location that is not visible by the user wherein different tones are emitted based on an angle of the barbell. FIG. 9 shows a barbell on the floor, a setup typical for dead lifts, shrugs, curls, back pulls and other various exercises.

Figure 10:
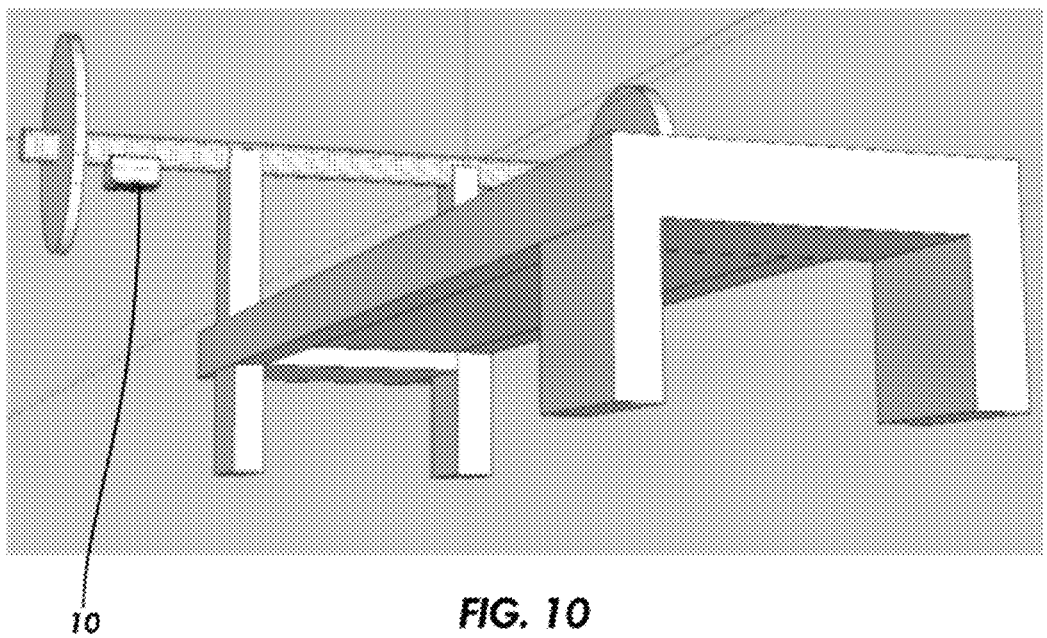
FIG. 10 illustrates where to place the barbell level indicator when performing a bench press exercise according to one embodiment of the disclosure.

FIG. 10 illustrates where to place the barbell level indicator when performing a bench press exercise. Notice the space between the bench support and the barbell level indicator. That space is used for the user's hand placement. The indicator LEDs are facing down for easy viewing when using the bench. The barbell level indicator is preferably placed on either side to prevent the indicator from contacting the chest of a user during exercise.

Figure 11:
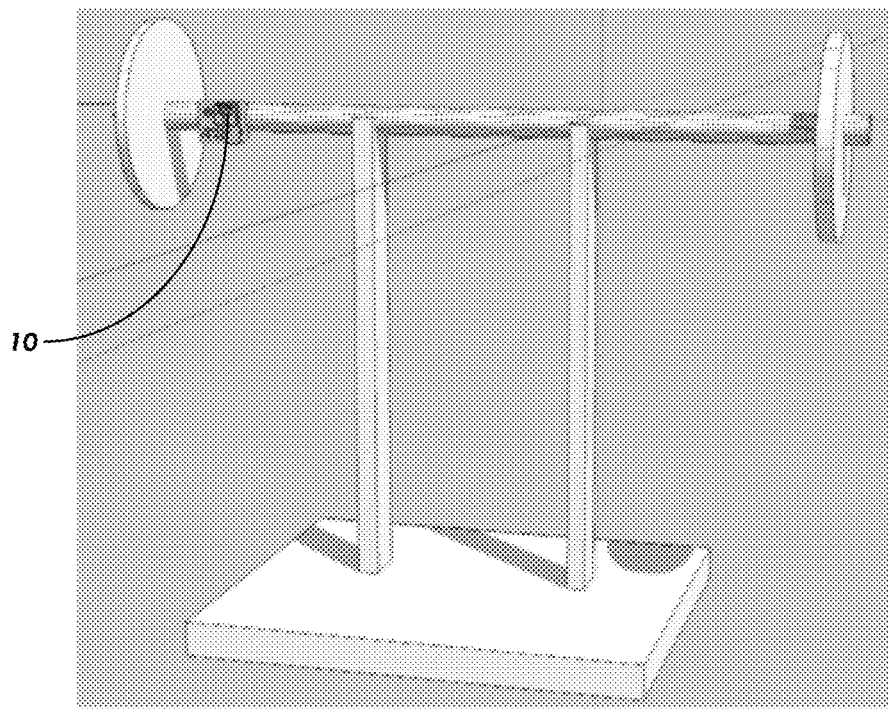
FIG. 11 illustrates the placement of the bar level indicator facing front on a barbell resting on a squat rack or military press bench (squat rack shown) according to one embodiment of the disclosure.
Figure 12:
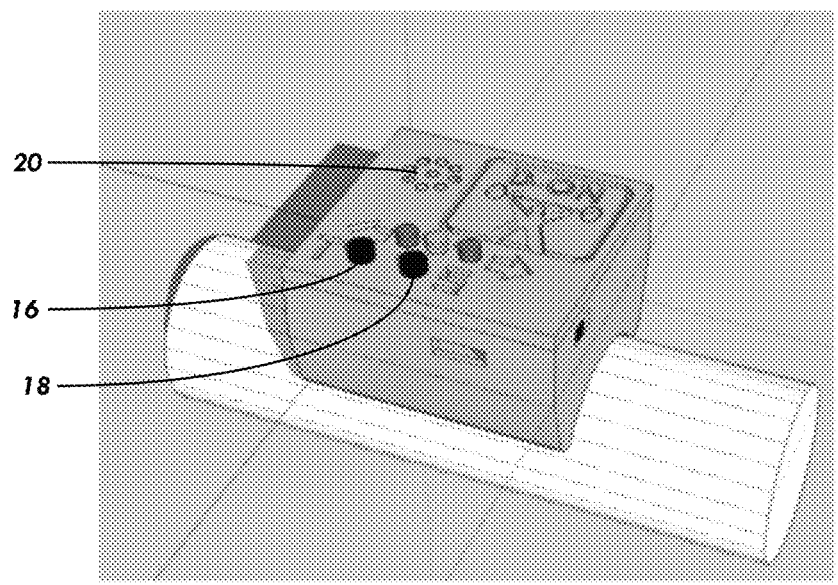
FIG. 12 illustrates the barbell level indicator secured to a curved surface, such as the handle of a barbell, according to one embodiment of the disclosure.

FIG. 11 illustrates a placement of the bar level indicator facing front on a barbell resting on a squat rack or military press bench (squat rack shown). The barbell level indicator LEDs can be seen from a mirror or the audible alarm may also be used as an indicator.

When the bar level indicator is placed on a bar cleared from the body and ready, the user should turn on the barbell level indicator and press any button to wake the system. To calibrate the user presses the S button. If S is not pressed, the accelerometer will automatically default to 0 degrees. After the S button is pressed a beep will be emitted indicating that the calibration button is finished. The user should set the tolerance level by pressing the T button. Every time the T button is pressed audible tones proportional to the tolerance level are emitted. Tol1 no tone, tol2 one tone, tol3 two tones, tol4 three tones and then roll back to tol1 no tone. The tolerance sensitivity will vary from user and exercise.

If sound alarms need to be disabled, hold the S button for 3 seconds until the device beeps. Once in silent mode, only the LEDs will function. Tolerance settings and set points will still be audible.

To charge the barbell level indicator, it must be plugged into a USB micro B cable connected to a PC or charger capable of providing 5V DC. The charger should follow standard wiring. At least 100 mA of current is necessary to charge the device. If the device is on, the red LEDs will blink indicating charging and once charged the green LED will be lit and the others off. No other functionality may operate in this mode.

To retrieve data from the barbell level indicator 10 using a computer interface, connect the USB connector to a PC/Tablet/Mobile Device and start a software application. Next, press retrieve data, at which point numerous tools in the software can be used to analyze workouts or to share via social media. When the outside computer is connected, it will also time sync the barbell level indicator with the local clock.

Transferring Level Readings to PC, Tablet or Mobile Device

Another feature of the barbell level indicator 10 is a capability to transfer the level readings to a PC/Tablet or Mobile device such as an iPhone®, Android®, Windows Mobile®, or other like mobile devices for logging, graphing, analyzing or sharing workout level information over social medial such as Facebook, Twitter or Google+. A client PC application will request data from the barbell level indicator 10 using a communication interface such as Bluetooth or USB. The client application will read the values using an emulated or virtual Com port or a virtual i2c protocol over real hardware modules capable of supporting USB or Bluetooth protocols on the chip. The application may be written in any programming language capable of sending serial data or calling a dynamic link library provided by the chip vendor such as an FTDI chip for USB to serial or i2c communications or a Bluetooth module such as SPBT2632C2A.AT2. The barbell level indicator will have an msp430 or a pic microchip microcontroller capable of receiving and sending data using UART such as 232 or synchronous serial communications such as i2c.

Additionally, the board will have a non-volatile memory storage inside a microcontroller of a different chip to store accelerometer values for later retrieval or to use as a buffer during faster exercises if needed.

The following sequence of steps illustration transferring level readings to a PC or other portable device. Data transfer can be performed in real time while exercising and also for later retrieval:

1. Barbell level indicator and PC tablet or mobile device paired over Bluetooth or connected using USB.
2. Client requests the data from the ftdi or Bluetooth chip, ftdi or Bluetooth module acknowledges microcontroller, microcontroller gets the non-volatile memory readings from the internal memory or request the data over i2c from a memory chip.
3. Memory chip or internal to the microcontroller reports back the readings, a timestamp appended to the readings by the microcontroller.
4. Microcontroller sends the data over UART low level or i2c to FTDI or Bluetooth module.
5. Client app receives the information.
6. Client converts the data to understandable readings (binary to decimal).
7. User decides to graph, save, compare or share over network.
8. Client app will also have the capability to sync times to barbell level indicator or to clear up sections or all the memory from the microcontroller internal memory or chip.
9. A GUI interface will either call a dynamic link library to send data over Bluetooth or USB. Android devices will use java application using the eclipse environment, Apple products will use objective C, Windows systems will use C# or visual basic. Linux will use python. To share data over social medial, Facebook sdk, Google+ sdk and Twitter SDK can be used.
10. Software reads values of inclination and acceleration. The device includes a calibration button, tolerance, graphs, load history, options for sharing to social media, discover Bluetooth device functions, and alarm options. The software is also capable of changing sounds or adding voice commands for alerting a user of improper technique detected by the barbell level indicator 10, achievement of goals, record keeping, elapsed time of a workout, repetition time, proper acceleration of a weight lifting movement and counting total repetitions.

In operation, the barbell level indicator 10 is connected to a barbell, weight, or other exercise apparatus. After connecting the barbell level indicator 10 to the barbell, the indicator is calibrated such that an initial position of the barbell level indicator 10 is stored. A user may program a desired tolerance of the barbell level indicator 10 such that the buzzer alarm is only activated if a position of the barbell exceeds the tolerance entered by the user. For example, a user may enter a tolerance of approximately 15° of tilt such that if the barbell exceeds that angle the buzzer alarm is activated.

As the user performs exercises with the barbell, the barbell level indicator 10 evaluates a position of the barbell and alerts the user if the barbell exceeds the tolerance entered by the user. Further, in the embodiment wherein a Bluetooth module communicates with a mobile device of the user, information is transmitted and stored related to the user's workout such as a number of repetitions, repetition rate, length of workout, and other various parameters measured that allows a user to analyze a workout after the workout occurs.

For example, the accelerometer of the barbell level indicator measures data related to movement and an orientation of a barbell and transmits that data to the microprocessor where the data is stored and optionally transmitted to a user's mobile device. For example, data captured by the accelerometer could correspond to a user performing a bench-press exercise, wherein the accelerometer detects an acceleration of a barbell as it descends towards a user followed by a deceleration as a barbell reaches a point adjacent a user's chest, followed by an additional acceleration as the user pushes a barbell away from the user's chest. A number of repetitions may be tracked by evaluating acceleration events and a direction of acceleration as detected by the accelerometer to determine when a full repetition occurs.

Figure 20:
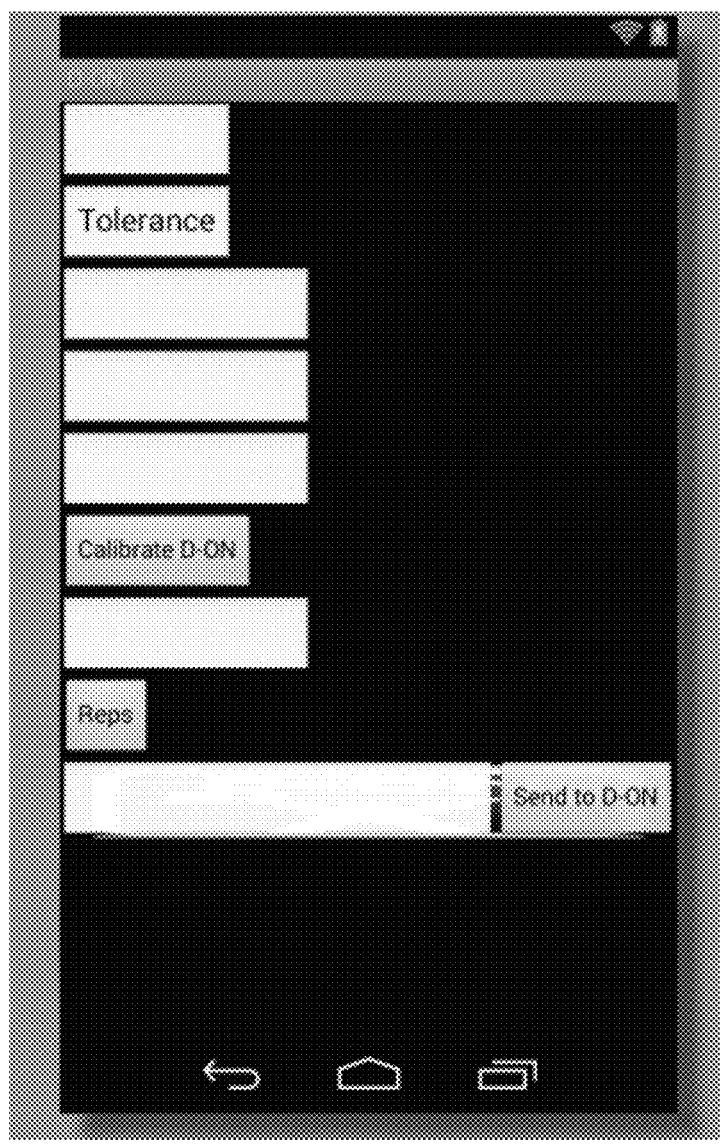
FIG. 20 illustrates a graphical user interface of a barbell level indicator according to one embodiment of the disclosure.

When the barbell level indicator is paired with a mobile device via the short-range communications module, such as a Bluetooth® transmitter, a user may input data to the barbell level indicator through a graphical user interface of the mobile device. As shown in FIG. 20, the graphical user interface may include various input fields such as tolerance levels and a number of repetitions. The graphical user interface may further enable a user to calibrate the accelerometer of the barbell level device by pressing a calibrate button. Data entered through the graphical user interface may be transmitted to and stored on the barbell level indicator. Additionally, data received from the barbell level indicator on the mobile device may be stored on the mobile device and further shared via social media, e-mail, text, or other communication tools, thereby allowing a user to share and track data related to a particular workout involving the barbell level indicator.

The barbell level indicator 10 of the present disclosure advantageously enables a user to improve the user's posture during exercise and alert the user to any incorrect posture or out of balance barbell during an exercise. The user may also track and store records such as a number of repetitions completed over a given period of time, as well as a number of repetitions corresponding to a particular weight of the barbell.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A barbell level indicator for detecting movement of a barbell, the barbell level indicator comprising:
    a housing shaped to fit adjacent a barbell;
    one or more magnets positioned within the housing for securing the housing to the barbell;
    an accelerometer secured within the housing
    an alarm; and
    a microprocessor located within the housing and in electronic communication with a memory, the accelerometer, and alarm for:
        receiving acceleration data and data related to an angle of the barbell level indicator from the accelerometer and storing accelerometer data on the memory;
        determining the angle of the barbell level indicator with the microprocessor based on accelerometer data stored on the memory;
        storing a limit angle on the memory; and
        emitting a warning on the alarm when the angle of the barbell level indicator is determined by the microprocessor to exceed the limit stored on the memory.

2. The barbell level indicator of claim 1, further comprising a short-range communications module in electrical communication with the microprocessor for transmitting data related to the angle and movement of the barbell level indicator from the accelerometer to a mobile device.

3. The barbell level indicator of claim 1, wherein the alarm comprises an audible alarm configured to emit an audible signal when the angle of the barbell level indicator is greater than the limit angle.

4. The barbell level indicator of claim 2, wherein the alarm comprises one or more visual indicators configured to illuminate when the angle of the barbell level indicator is determined by the processor to be greater than the limit angle stored on the memory.

5. The barbell level indicator of claim 4, wherein the alarm further comprises one or more LED lights configured to illuminate when the angle of the barbell level indicator is greater than the limit angle.

6. The barbell level indicator of claim 3 further comprising a push button in electrical communication with the microprocessor for calibrating an initial angle of the barbell level indicator.

7. The barbell level indicator of claim 2, wherein the short-range communications module comprises a Bluetooth® transmitter.

8. A barbell level indicator for detecting movement of a barbell, the barbell level indicator comprising:
    a housing shaped to fit adjacent a barbell, the housing including a concave bottom portion shaped to adapt to the barbell;
    one or more magnets positioned within the housing and along the concave bottom portion of the housing for securing the housing to the barbell;
    an accelerometer secured within the housing;
    an alarm;
    a microprocessor located within the housing and in electronic communication with a memory, the accelerometer, and alarm for:
        receiving acceleration data and data related to an angle of the barbell level indicator from the accelerometer and storing accelerometer data on the memory;
        determining with the microprocessor a number of repetitions of an exercise with the barbell based on the accelerometer data measured by the accelerometer and stored on the memory;
        determining a angle of the barbell level indicator with the microprocessor based on data related to the angle of the barbell level indicator stored on the memory;
        storing a limit angle on the memory;
        emitting a warning on the alarm when the angle of the barbell level indicator is determined by the microprocessor to exceed the limit angle stored on the memory;
    a short-range communications module in electrical communication with the microprocessor for transmitting the data related to movement of the barbell from the accelerometer to a mobile device.

9. The barbell level indicator of claim 8, wherein the alarm comprises a buzzer alarm configured to emit an audible signal when the angle of the barbell level indicator is greater than the limit angle.

10. The barbell level indicator of claim 8, wherein the alarm comprises one or more LED lights configured to illuminate when the angle of the barbell level indicator is greater than the limit angle.

11. The barbell level indicator of claim 1, further comprising determining with the microprocessor a number of repetitions of an exercise with the barbell based on acceleration data measured by the accelerometer and stored on the memory corresponding to raising and lowering of the barbell.

* * * * *